United States Patent [19]

Jones

[11] 4,021,298

[45] May 3, 1977

[54] CONVERSION OF COAL INTO HYDROCARBONS

[75] Inventor: Andrew R. Jones, Murrysville, Pa.

[73] Assignee: Westinghouse Electric Corporation, Pittsburgh, Pa.

[22] Filed: Jan. 29, 1974

[21] Appl. No.: 437,575

[52] U.S. Cl. .................................. 176/39; 176/60; 176/65; 260/451; 252/373; 423/655; 48/196 R
[51] Int. Cl.² ..................................... G21C 15/00
[58] Field of Search ................. 176/39, 60, 65; 260/449, 451; 252/373; 423/650–655; 48/196 R

[56] References Cited

UNITED STATES PATENTS

| 2,904,483 | 9/1959 | Long et al. | 176/39 |
| 2,958,637 | 11/1960 | Voorhees | 176/39 |

OTHER PUBLICATIONS

Chem. Eng., New Use of Nuclear Energy, Aug., 1955, pp. 132–134.

*Primary Examiner*—Samuel Feinberg
*Assistant Examiner*—Peter A. Nelson
*Attorney, Agent, or Firm*—Z. L. Dermer; E. L. Levine

[57] ABSTRACT

Hydrocarbons are formed of coal and water. The water is converted or dissociated separately into hydrogen and oxygen in a first chemical reactor by thermochemical and/or electrolytic processing. The resulting hydrogen is then reacted with the coal in a second reactor to produce the hydrocarbons. Residual carbon from the second reactor is reacted in a third reactor with oxygen derived from the first reactor to produce carbon monoxide. The carbon monoxide is reacted with residual hydrogen from the second reactor or hydrogen from the first reactor to produce additional hydrocarbons. The energy for the endothermic and/or electrolytic processing in the reactors and for auxiliary equipment of the apparatus is supplied by a very high-temperature, gas-cooled, nuclear reactor by heat interchange with the cooling gas, helium. The cooling gas operates through heat-exchange means which isolates the cooling gas from the processing apparatus.

5 Claims, 15 Drawing Figures

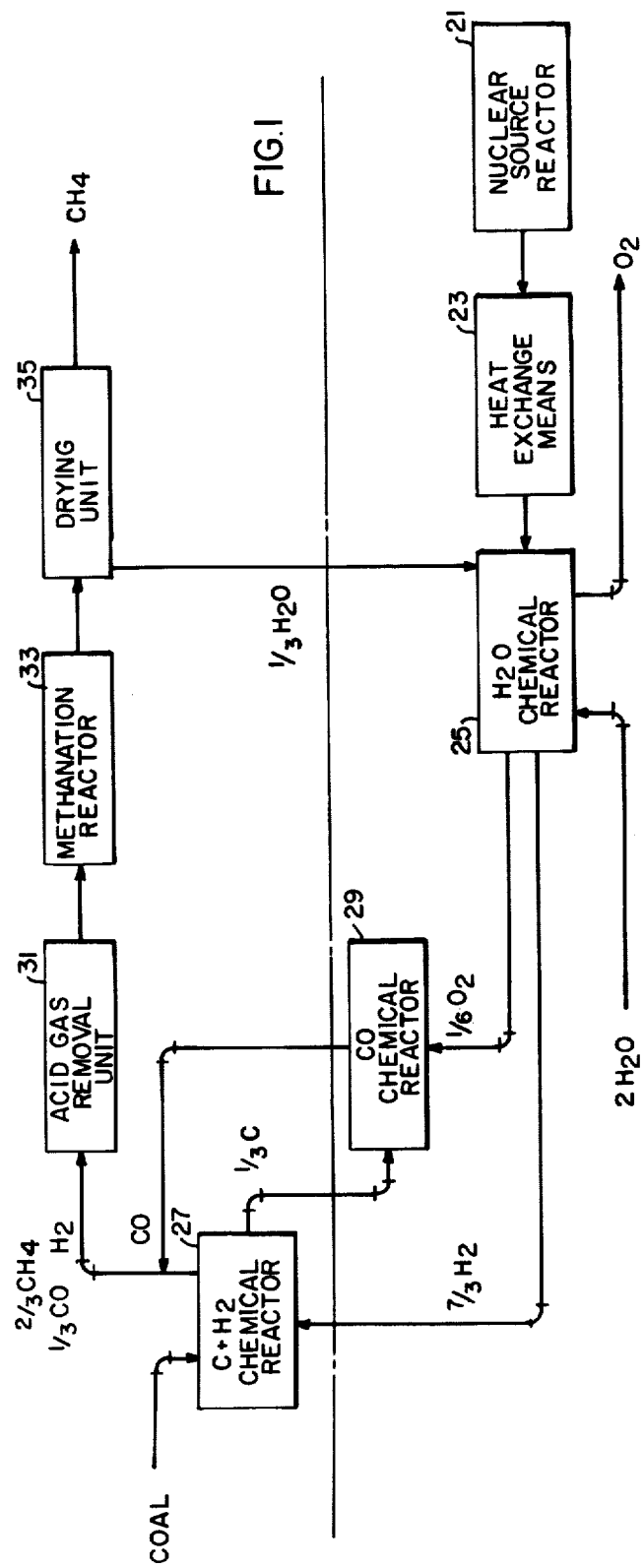
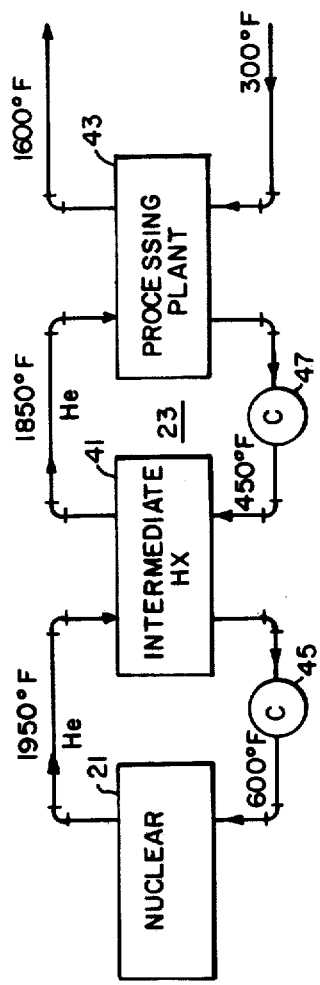

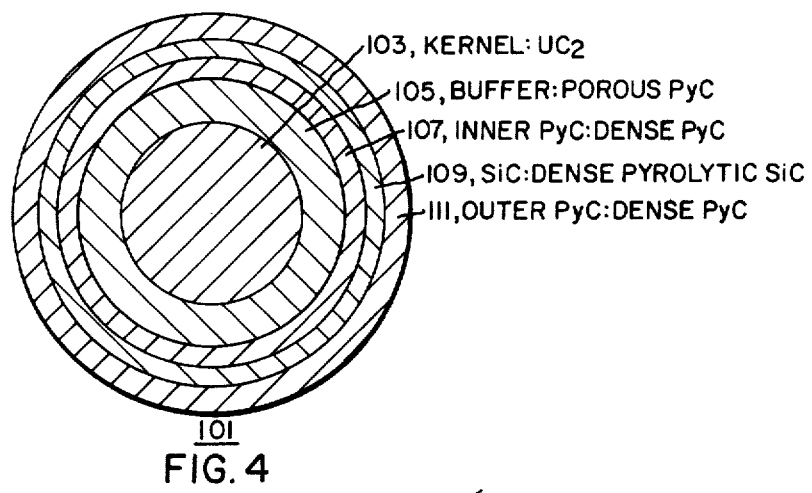
FIG. 4
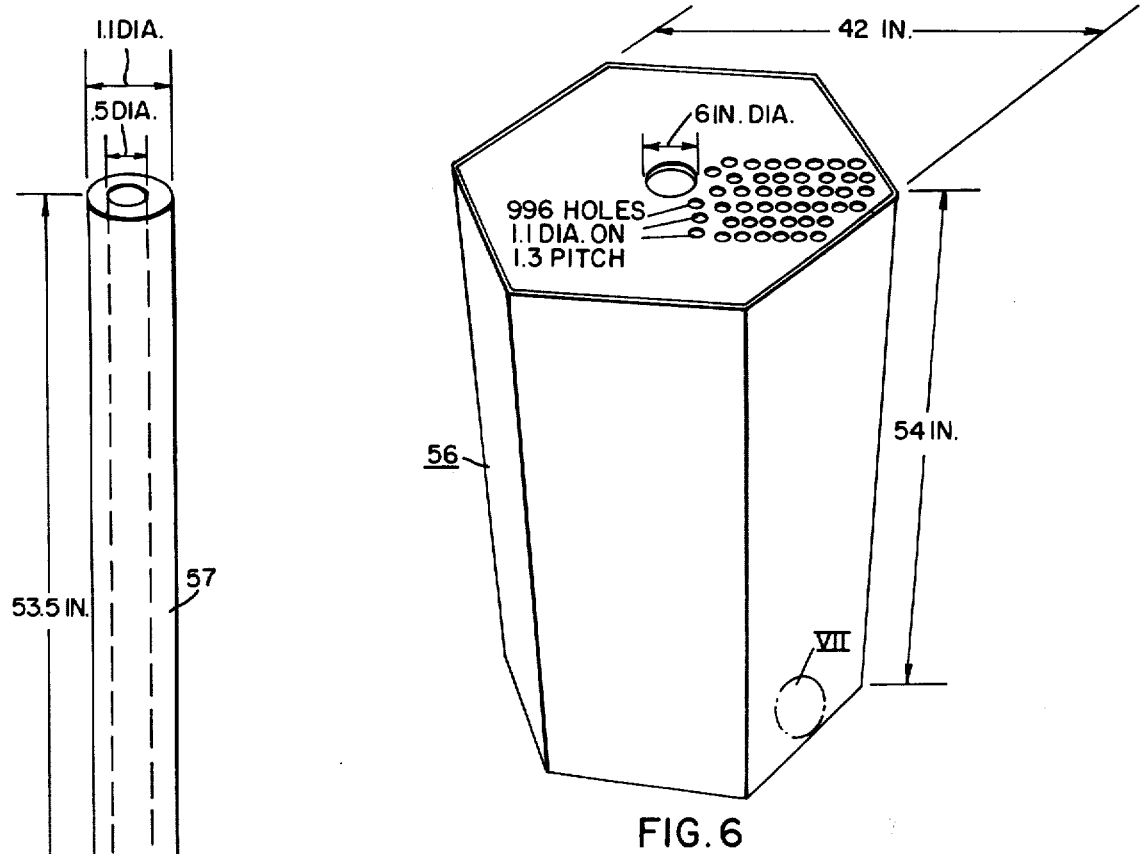
FIG. 5
FIG. 6
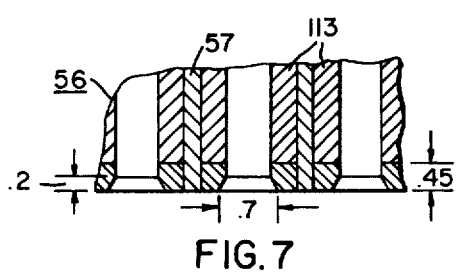
FIG. 7

CONVERSION OF COAL INTO HYDROCARBONS

REFERENCE TO RELATED DOCUMENTS

1. Application Ser. No. 437,571 now U.S. Pat. No. 3,888,750, filed concurrently herewith to Lee E. Brecher and Christopher K. Wu for *Decomposition Of Water* (herein called Brecher application) and assigned to Westinghouse Electric Corporation.
2. G. Alex Mills — *Progress in Coal Gasification* — Proc. Third SNG Symposium, 1970.
3. H. A. Shearer — *The COED Process Plus CHAR Gasification* — Chemical Engineering Progress, Vol. 69, No. 3. Mar. 1973.
4. R. J. Bard — *Coated Particle Fuel Element for UHTREX*, CMB-8-4008, May 1965.
5. Journal of Chemical Physics, Vol. 36, No. 4 (1961).
6. A. B. Wahlin — *Transmission of $H_2$ Through Metals*, Journal of Applied Physics 1951 (1503). Documents 4 and 5 relate to the diffusion of hydrogen during transmission.

BACKGROUND OF THE INVENTION

This invention relates to the conversion of coal into hydrocarbons, sometimes referred to as gasification or liquefaction of coal, and has particular relationship to such conversion by reactions involving principally coal and water. These reactions, in whatever way they are carried out, demand substantial quantities of energy; in addition some of the coal reacted may be dissipated in waste products. At the cost of this energy and the dissipated coal the remaining coal is converted into a more useful gaseous or liquid form.

The prior art relating to the conversion or gasification of coal is typified by the following processes:

HYGAS developed by the Institute of Gas Technology.
BI-GAS developed by Bituminous Coal Research.
The Lurgi widely used in Australia, South Africa and Germany.
COED (Char Oil Energy Development) developed by FMC Corporation supported by the Office of Coal Research (See Document 2).
SYNTHANE developed by the Bureau of Mines.
Kellog developed by M. W. Kellog Co.
$CO_2$ Accepter developed by Consolidate Coal Company.
H-Coal, a liquefaction process, developed by Hydrocarbon Research Inc., funded by the Office of Coal Research.
Hydrodesulfurization, also liquefaction, developed by the Bureau of Mines.
COG (Coal-Oil-Gas Refinery), also liquefaction, Investigated by Chem Systems, Inc. and Pittsburgh and Midway Coal Mining Company.
Methanol, also liquefaction.

In these prior-art processes steam is mixed at one stage or another with the coal. The coal reacts with the steam, part of the coal is converted into a hydrocarbon, usually $CH_4$, but a substantial part of the coal is converted into carbon dioxide which is exhausted into the coal and the less-active fraction is reacted with steam to produce additional hydrogen for the hydrogasification and carbon dioxide. Where coal is used to supply the energy for the processes there is a depletion of the coal in addition to the loss by dissipation. Prior-art conversion process have then suffered from the disadvantage that their use of the coal has not been efficient.

It is an object of this invention to overcome the above-described disadvantage of the prior-art processes for converting coal into hydrocarbons and to provide apparatus and a method for effecting such conversion in the use or practice of which the fraction of the coal converted into hydrocarbons shall be maintained and the fraction of the coal which is consumed without being converted or is dissipated shall be minimized.

SUMMARY OF THE INVENTION

A typical chemical reaction describing the conversion of coal and water into methane, in accordance with the teachings of the prior art, where the energy for the conversion is derived by burning coal, is:

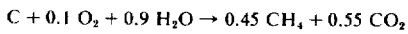

$$C + 0.1\ O_2 + 0.9\ H_2O \rightarrow 0.45\ CH_4 + 0.55\ CO_2$$

This reaction takes place in the SYNTHANE process. In this case a maximum of only 45% of the coal can be converted into usable hydrocarbon. Another such prior-art conversion process is described by the equation

$$C + 0.259\ O_2 + 0.742\ H_2O \rightarrow 0.371\ CH_4 + 0.630$$

In this case a maximum of only 37% of the coal can be converted into methane. Where the energy for the conversion is derived from a nuclear reactor, the reaction is typically:

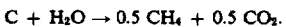

$$C + H_2O \rightarrow 0.5\ CH_4 + 0.5\ CO_2.$$

In this case a maximum of only half of the coal can be converted into methane.

In accordance with this invention the fraction of coal converted into hydrocarbons is maximized by dissociating or converting the water into separate batches or streams of hydrogen and oxygen separately from the coal and then reacting the hydrogen so derived with the coal. The oxygen derived from the conversion of the water is in part reacted with residual coal or char from the prior hydrogen reaction, to form carbon monoxide which is then further reacted with hydrogen to form additional hydrocarbon. The oxygen may also be used in the process to form methanol ($CH_3OH$) and excess oxygen and any excess hydrogen may be sold. There is urgent demand for oxygen in large quantities in many areas such as for disposal of sewage which has become a burgeoning problem and industries such as steel making. The energy for the conversion, including endothermic reaction demands and the demands of the auxiliary apparatus, is relatively low-cost nuclear energy, preferably derived from a very high-temperature, gas-cooled, nuclear reactor.

Water is converted into hydrogen and oxygen by electrolytic or thermochemical methods or methods $$H_2O \rightarrow H_2 + \tfrac{1}{2} O_2.$$

It is an endothermic reaction demanding substantial energy which is supplied by the nuclear reactor. The reaction of the coal (carbon) and the hydrogen is:

$$C + 2 H_2 \rightarrow CH_4.$$

It is a slightly exothermic reaction. The reaction between oxygen and the residual coal is:

$$2C + O_2 \rightarrow 2 CO.$$

This reaction is exothermic and may supply heat for other purposes in the process. The reaction between the carbon monoxide and the hydrogen is $$CO + 3 H_2 \rightarrow CH_4 + H_2O$$

and is also exothermic.

It is contemplated that the process according to this invention will make hydrogen and oxygen available at a substantially lower cost than at present. Typical cost, in large quantities, of hydrogen at present is 36 cents per 100 cubic feet and of oxygen 10 cents per 100 cubic feet. There is also a rental charge of $11.50 per month for a 1400 gallon bottle. It is anticipated that hydrogen would be produced in the practice of this invention under current cost conditions at 15 cents per 1000 cubic feet and oxygen at 4 cents per 1000 cubic feet.

An important advantage of this invention is that in its practice coal is conserved. Since the coal required per unit hydrocarbon product is reduced in the practice of this invention, the following additional advantages flow from this invention:

1. Mine life or production capability is increased.
2. Additional mining sites not feasible for the prior-art processes can serve for the practice of this invention.
3. Environmental pollutants such as ash and $CO_2$ are reduced by as much as one-half to two-thirds.
4. The cost of such hydrocarbons as synthetic crude oil, pipeline quality methane, methanol, ethylene and the like is substantially reduced.
5. The cost of on-site power at the processing plant is reduced.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which:

FIG. 1 is a block flow diagram showing the process and the apparatus according to this invention;

FIG. 2 is a block diagram showing the relationship of the nuclear reactor, the heat-transfer means and the processing chemical reactor plant of the apparatus shown in FIG. 1;

FIG. 4 is a view in section of a bead constituting a

FIG. 6 is a view in perspective of a moderator block, including the fuel elements, of the reactor shown in FIG. 3;

FIG. 7 is a fragmental view in section of the portion in the circle VII of the block shown in FIG. 6;

FIG. 1 shows apparatus for converting coal and water into hydrocarbons and includes a nuclear reactor 21, heat-exchange means 23, and an $H_2O$ chemical reactor 25. As shown, water is supplied to the chemical reactor 25 and is converted by this reactor into hydrogen and oxygen. The apparatus shown in FIG. 1 also includes a chemical reactor or gasifier 27 for reacting coal with hydrogen from the chemical reactor 25 to produce hydrocarbons. In the interest of concreteness, it will be assumed that the apparatus converts the coal and hydrogen into methane. There is also a CO-chemical reactor 29. Residual coal or char flows from chemical reactor 27 into chemical reactor 29 and reacts with oxygen supplied from chemical reactor 25 to produce carbon monoxide. The apparatus includes an acid gas removal unit 31. Methane and hydrogen from chemical reactor 27 and carbon monoxide from chemical reactor 29 flow through unit 31 into a methanation reactor 33. The unit 31 principally removes gaseous sulfur compounds from the mixture of gases which it receives but in addition it removes any carbon dioxide which may have been formed. Methanation reactor 33 completes the methanation of the coal. The resulting methane is then passed through a drying unit 35 into the pipe lines for distribution.

Figure 3:
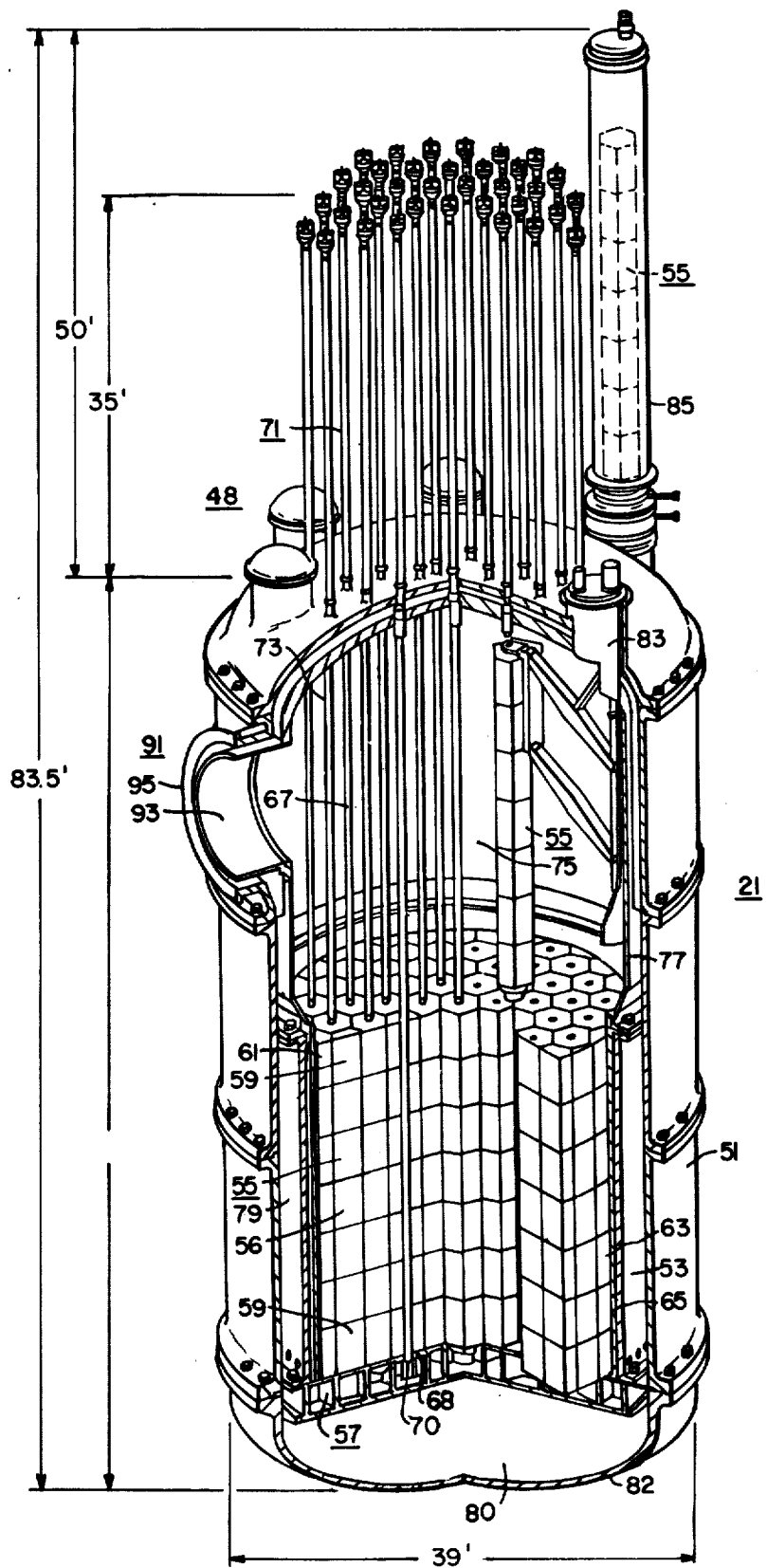
FIG. 3 is a view in perspective, with a portion of the wall broken away, of a typical reactor included in apparatus in accordance with this invention.

The heat-exchange means 23 is shown in FIG. 1 interposed in a simple manner between the nuclear reactor 21 and $H_2O$-chemical reactor 25. In actual practice the interconnection is more complex as the chemical reactor 25 includes a plurality of components which operate at different temperatures and demand different quantities of heat. The connection shown between the means 23 and the chemical reactor 25 represents these multiple interconnections. The more complex interconnection is shown in FIG. 2. Here there is included an intermediate heat exchanger 41 which isolates the fluid from the nuclear reactor 21 from the remainder of In addition, energy is supplied by the nuclear reactor 21 for the auxiliary functions of the apparatus such as pulverizing the coal, volatilizing its volatile products, pumping of fluids, producing fluid beds of the coal, for example in chemical reactor 27, and drying. The connections for supplying this energy are not shown in FIG. 1.

In the use of the apparatus shown in FIG. 1 the coal is pulverized, seived and dried and fed by a conveyor (not shown) or through a hopper into $C + H_2$ chemical reactor 27. Here the gaseous products are volatilized from the coal and transmitted to acid removal unit 31. The resulting carbon is reacted with the hydrogen from the $H_2O$-chemical reactor 25 to produce methane and the methane and excess hydrogen are transmitted to unit 31. Typically the hydrogen is supplied from the chemical reactor 25 at a pressure of about 250 lbs. per sq. in. The pressure is increased to 3000 psi by a compressor (not shown in FIG. 1) and delivered at this higher pressure to the chemical reactor 27. The residual carbon is transmitted to chemical reactor 29 to produce carbon monoxide which is also transmitted to unit 31.

The heat or energy source 21 is a nuclear reactor source. This source 21 includes one or more reactors preferably of the gas-cooled type and it supplies a gas, which is typically and preferably helium, but may be other gases such as argon, or even nitrogen, at a high temperature of about 2000° F. The temperature of the heating gas circulated by the circulators 45 and 47 (FIG. 2) among the nuclear reactor 21, the intermediate heat exchanger 41 and the heat exchangers 43 of the processing plant is shown in FIG. 2. It is contemplated that in the nuclear reactor 21, the gas may reach a peak temperature of about 2200° F.

The energy of the source 21 which is required to produce the conversion of water into hydrogen and oxygen can be computed as follows:

---
Energy required to convert 1 lb. of $H_2O$ - 6830 BTU
No. of lbs. $H_2O$ for 1000 cu. ft. of $H_2$
under standard conditons -50.4
No. of BTU in one megawatt hr. (MW HR) - $3.1413 \times 10^6$
No. of MWHR for 1000 cu. ft. of $CH_4$ =
$$\frac{\frac{6830}{N_H} \times 50.4 \times 2}{3.1413 \times 10^6} = \frac{.2192}{N_H}$$
---

$N_H$ is the thermal efficiency of the water conversion process and the factor of 2 is included because there are 2 moles of hydrogen in each mole of $CH_4$.

Where $500 \times 10^6$ SCF (cu. ft. under standard conditions) of $CH_4$ are to be produced per day the rating of the source 21 is $$\frac{.2192 \times 500 \times 10^6}{1000 \times 24 \, N_H} = \frac{4567}{N_H} \, MW$$

If the efficiency is about 50%, 9134 MW would be required and for an efficiency of 60%, 7612 MW would be required. The thermal rating for a reactor presently permitted by the AEC is 3800 MW. Probably in either event three reactors would be required since energy is required not only for the water conversion but also for the auxiliary functions.

A typical nuclear reactor 48 (FIGS. 3–7) includes a pressure vessel 51. Within the vessel 51 there is a core barrel 53. Centrally within the barrel are removable fuel modules 55. Each module 55 is formed of a column of moderator blocks 56 (FIG. 6) containing the fuel elements 57 (FIG. 5) with removable neutron reflector blocks 59 at the top and bottom. The modules 55 are encircled within the core barrel 53 by permanent neutron reflectors 61. Around the reflectors 61 there are cooled slats 63 and thermal insulation 65. The core components 55, 59, 61 are mounted on core-support plate 57. The reactivity control for shutdown, scram and operation is effected by control rods 67 which penetrate through each column 55. When the control rods 67 are dropped to the lowermost position, they penetrate through an orifice plate 68 above the support plate 57 and engage a shock absorber 70. The rods 67 are connected to drive mechanisms 71 by respective drive shafts 73 which pass through the pressure vessel 51. The exit plenum 75 from which the cooling gas heated by the core is conducted is defined by exit-plenum liner 77 which is secured to, and extends from, the barrel 53. There is an annular volume 79 bounded by the inner surface of the pressure vessel 51, the barrel 53 and the liner 77 which extends from it. This volume 79 is in communication with the inlet plenum 80 between the support plate 57 and the base 82 of the vessel 51. Above the core 55-59-61 is a volume, forming the exit plenum 75, approximately equal to the core volume to provide space for refueling. The fuel handling machine 83 is installed into the space 75 through three ports (not shown) for maintenance of the reactor while shut down. There are a plurality of (usually 3) fuel transfer cakes 85 equally spaced around the periphery of the pressure vessel 51. The removal of selected core or reflector columns 55 or 59 from the core is accomplished by the control-rod drive mechanisms 71 which elevate the columns 55, 59 to the level of the fuel handling machine 83. The fuel handling machine then transfers the fuel column 55 to one of the three fuel transfer casks 85.

The ports 91 on the nuclear reactor 48 are concentric ducts formed of an inner duct 93 and an outer duct 95. The high temperature gas exiting from the reactor 49 passes through the inner duct 93 and the lower temperature gas returning to the reactor 21 passes through the annulus between the outer duct 95 and the inner duct 93. The flow of the gas is shown by arrows. The colder gas traverses the entire annulus 79 of the pressure vessel 51 prior to entering the core inlet plenum 80. This feature along with low core inlet temperature minimizes the need for complex pressure vessel cooling circuitry and insulation. The exit plenum liner 77 and exit duct 93, as well as the control rods 73, are cooled by the inlet gas. Moreover, since parts 91 are exposed only to the low core pressure drop and are not primary structural members, high margins of safety for long life operation are assured. The parts of the nuclear reactor 48 subject to the highest stress are cooled by the entrance gas. The exit gas from the reactor 48 is as indicated at a temperature of about 1950° F and at a pressure of between 800 and 1000 psi.

The basic structural fuel particle of the nuclear reactor 48 is a bead 101 typically having a diameter of about 440 microns. The bead 101 is formed of the following concentric components:
  kernel 103, enriched $UC_2$, diameter 200 microns;
  buffer shell 105, porous pyrolytic carbon (1.15 g/cm³), thickness 48 microns;

inner shell 107, dense pyrolytic carbon (1.95 g/cm³), thickness 22 microns;

intermediate shell 109, dense pyrolytic siliconcarbide (3.2 g/cm³), thickness 20 microns;

outer shell 111, dense pyrolytic carbon (1.8 g/cm³), thickness 30 microns.

A mass of the beads 101 is thoroughly mixed with graphite and an alcohol binder and extruded into a hollow cylinder 57 (FIG. 5). In the blocks 56 the cylinders 57 are inserted between graphite sleeves 113. The beads 101 retain fission products. Their rupture during the extrusion and in subsequent use is minimal so that the contamination of the cooling gas by radioactive materials is minimal.

The reactor coolant gas passes directly over the surface of the fuel elements thus minimizing the temperature difference between the fuel 57 and the coolant, and a lower temperature of fuel is required for a desired temperature of coolant. Typically, in the practice of this invention, a nominal maximum fuel temperature of 2260° F is adequate to produce a coolant temperature of 1950° F. Where the fuel element is indirectly cooled to a maximum fuel temperature of 2500°–2750° F is required for a temperature of only 1400° F for the coolant.

Figure 10:
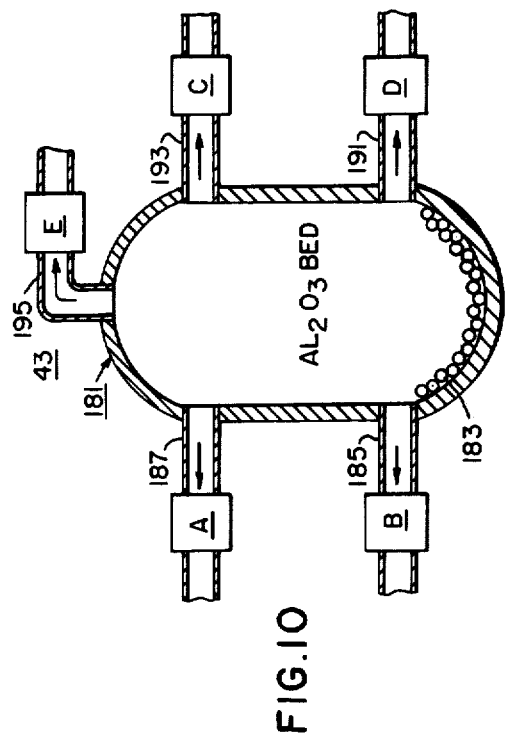
FIG. 10 is a view in section generally diagrammatic of a typical process heat exchanger unit included in the apparatus shown in FIG. 1.

The typical intermediate heat exchanger 41 (FIG. 2) shown in FIG. 10 includes a generally cylindrical pressure vessel 121 having end bells 123 and 125. Within the vessel there are a plurality of tubes 127 supported on tube sheets 129 and 131. The upper end bell 123 has a port 133 from which coaxial ducts 135 and 137 extend. A bell-shaped shell 139 supported between the inner duct 137 and the upper tube sheet 129 extends generally parallel, and coaxial with, the end bell 123 defining an annular volume 138 between it and this end bell 123. At least one side port 141 extends into the vessel 121. This side port 141 includes coaxial outer duct 143 and inner duct 145 which are coextensive with the ducts 95 and 93 (FIG. 5) respectively of the reactor 48. The inner duct 145 is connected to the parts 147 and 149 of a shell coaxial with the vessel 121. The part 147 of the shell extends between the tube-sheet 129 and the upper part of the inner duct 145 and the part 149 of the shell is suspended from the lower part of the inner duct 145 and defines a narrow volume 151 between it and the tubes 127.

Adjacent the outer duct 143 there is a coaxial shell 153 terminating in bellows 155 connected to the outer duct 143 by a lip 157. The bellows 155 is connected to the outer duct 143 by a lip 157. The bellows 155 is connected to the parts 159 and 161 of another shell coaxial with the vessel 121. The upper part 159 of the shell is supported between the tube sheet 129 and the upper part of the shell 153; the lower part 161 of the shell terminates in a bellows 163 and is supported between the shell 153 and the lower tube-sheet 131. Additional support is provided by perforated lip 165 having the form generally of a truncated cone extending between the part 161 and the lower rim of the port 141.

The annular volume 138 is in communication with the annular volume 167 between the outer duct 143 and the shell 153, with the annular volume 169 between the shell part 161 and the vessel 121 and with the tubes 127. The space formed by these volumes 138, 167 and 169 is closed by the lip 157. As indicated by the arrows 171 the cooled gas (450° F) from the process flows through the annular volume between ducts 135 and 137 through the volume 138 and downwardly to the tubes 127 and then upwardly through these tubes. As indicated by the arrow 173 the hot gas (1950° F) from the nuclear reactor 48 flows through the inner duct 145 and down through the volume 151, counter to the flow of the cooled gas (450° F), and then, having been cooled to 600° F, back to the nuclear reactor 48, through the annular space between the inner duct 145 and the shell 153 as indicated by the arrows 175. The gas heated by the counterflow (at 1850° F) flows from the tubes 127 through the inner duct 137 to the process as indicated by the arrows 177. The bellows 155 and 163 and the lip 165 take up the stresses developed by the temperature differential between the hot gases. The gas from the reactor whose flow is shown by the arrows 173 and 175 is completely isolated by the heat exchanger 41 from the process gas whose flow is represented by the arrows 177 and 171. Typically a plurality of heat-exchangers 41 are operated in parallel to provide adequate hot gas for the processing. In a typical situation there are in all exchangers 59,500 tubes 127 spaced about 0.82 inch between centers presenting a heat-transfer surface area of 69,800 square feet.

Figure 9:
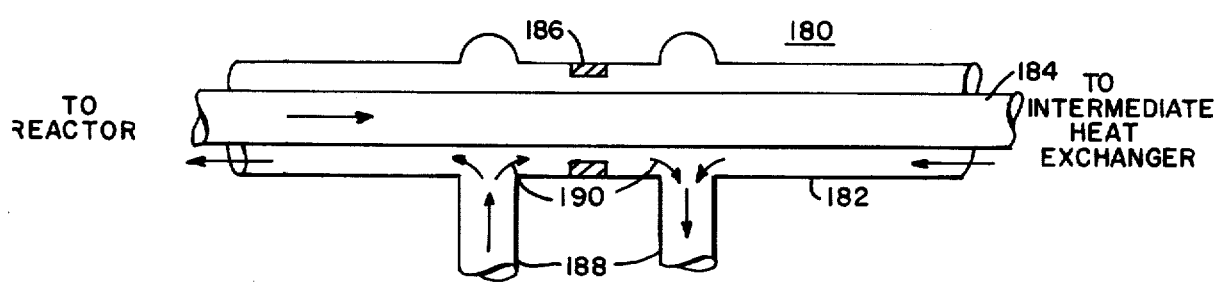
FIG. 9 is a fragmental view in section, generally diagrammatic, of a heat-transport duct of the apparatus shown in FIG. 1.

The gas between the reactors 48 and the intermediate heat exchanger 41 flows in coaxial ducts such as the ducts 180 of FIG. 9. The circulator 45 (FIG. 2) is tapped into the outer duct 182. To prevent the ducts 182 and 184 from being excessively stressed orifices 186 are interposed between the ducts 88 to the circulator 45 limiting back leakage as shown by the arrows 190 while permitting relative motion and minimizing stress build-up.

Figure 8:
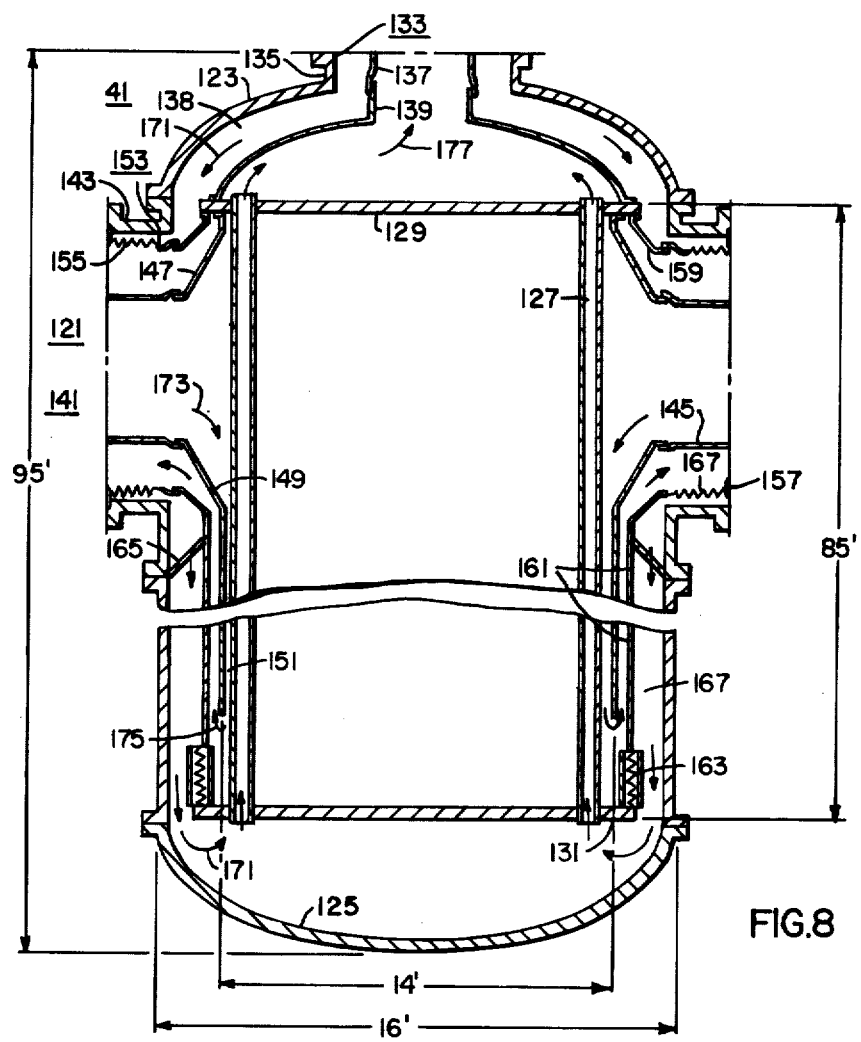
FIG. 8 is a view in vertical section of an intermediate heat exchanger of the apparatus shown in FIG. 1.

A typical processing heat exchanger 43 (FIG. 2) includes a vessel 181 (FIG. 10) containing a bed 183 of aluminum oxide. The vessel has an inlet duct 185 for the hot gas (1850° F) from the heat exchanger 41 and an outlet duct 187 for the cooled gas (450° F) returned to the heat exchanger 41. The ducts 185 and 187 are controlled by valves A and B and then these valves are connected respectively to the inner duct 137 and the outer duct 135 of the vessel 121 (FIG. 8). The vessel 181 also has inlet duct 191 and outlet duct 193 for the fluid to be heated in the vessel 181. Depending on the process for converting water into hydrogen and oxygen, this fluid is typically water combined with various chemicals such as Ca Br₂ and HI, or sulfuric acid. The ducts 191 and 193 are controlled by valves C and D. There is also an evacuating duct 195 controlled by valve E.

In the use of the heat exchanger 43, valves C, D and E are first closed and valves A and B are opened to admit hot gas (1850° F) to the vessel 181. After the Al₂O₃ bed 13 has reached the desired temperature, valves A and B are closed and, while valves C and D remain closed, valve E is opened and the gas is exhausted from the vessel 181, during a clean-up step, to a gas collector whence it is returned to heat exchanger 41. Next valve E is closed and, while valves A and B remain closed, valves C and D are opened admitting the fluid to be processed to the vessel 181 to be appropriately heated. After the processing is completed, valves C and D are closed and, while valves A and B remain closed, valve E is opened to carry out another clean-up step before a new cycle of operations.

Figure 11:
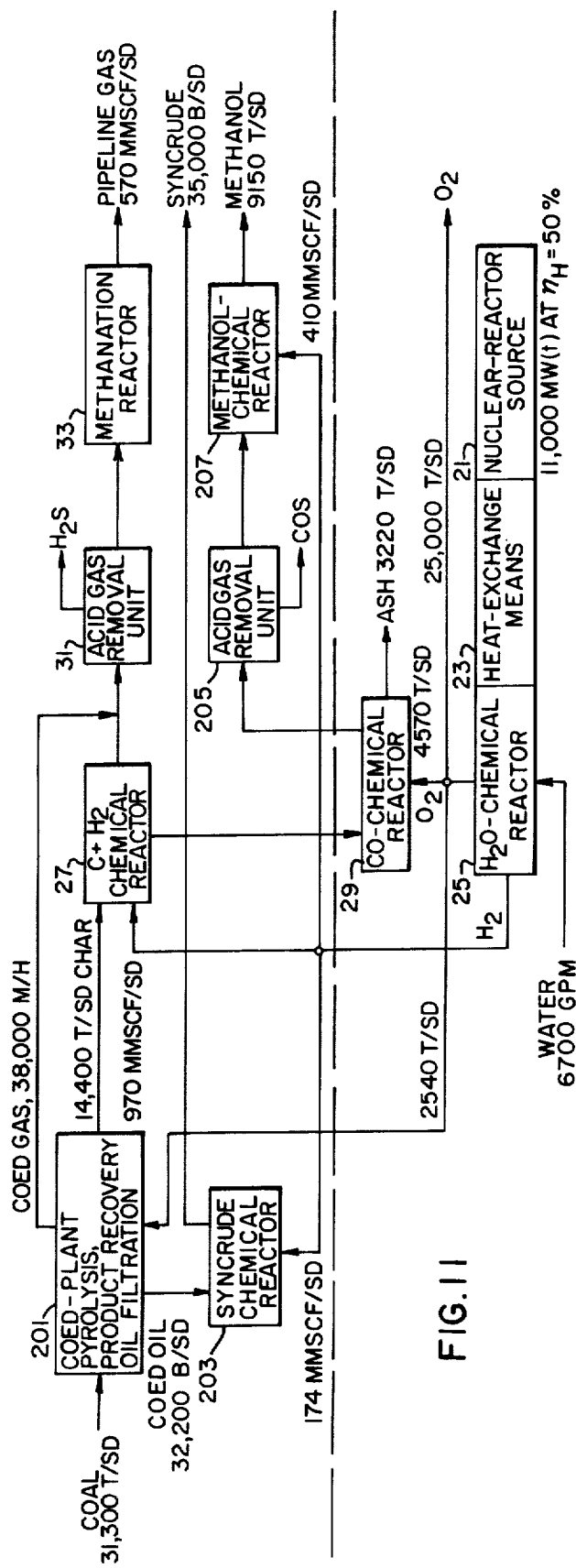
FIG. 11 is a block flow diagram for apparatus in accordance with this invention for producing a plurality of products in the practice of this invention.

In the complex shown in FIG. 11 water is converted into hydrogen and oxygen in the same manner as in the apparatus shown in FIG. 10. Typically, as indicated, for the conversion of 6700 gallons per minute and for the other purposes of the apparatus a nuclear-reactor source 21 capable of delivering 11,000 megawatts is demanded, assuming 50% efficiency. Before being subjected to the processing in accordance with this invention, the coal is subjected to the COED process in COED Plant 201. The coal, pulverized and dried, is pyrolized and its more volatile products are derived. The heat for this treatment may be produced by oxidizing a relatively small fraction of the coal under treatment. For this purpose oxygen is supplied from the chemical reactor 25. The energy for the COED plant 201 may be supplied by the nuclear-reactor source 21 instead. The oil derived from the COED plant 201 may be supplied by the nuclear-reactor source 21 instead. The oil derived from the COED plant 201 is treated with hydrogen from the $H_2O$-chemical reactor 25 in the syncrude chemical reactor 203 and collected for use. The char from COED-plant 201 is treated in the $C + H_2$ chemical reactor 27. Acid gas ($H_2S$) is removed from the resulting product by unit 31 and the resulting gas is methanated and dried in methanation reactor 33 and transmitted through pipe lines. Gas from the COED-plant 201 is similarly treated by unit 31 and reactor 33 and transmitted through the pipe lines. Carbon monoxide is produced in chemical reactor 29 by reacting residual char and oxygen. After acid gas (COS) removal by acid-gas removal unit 205, this CO reacts with hydrogen in methanol chemical reactor 207 to produce methanol.

Typical quantities of coal and products are shown on FIG. 11 adjacent the arrows indicating their flow. T/SD means tons per stream day; that is, per 24-hour day. Thus, typically 31,300 tons of coal per 24-hour day are treated in plant 201. B/SD means barrels per stream day. MMSCF/SD means million standard cubic feet per stream day, that is cubic feet under standard temperature and pressure conditions per 24-hour day. M/H means pound-moles per hour.

Industrially hydrogen has in the past been produced by electrolysis. Typical process based on processes are the Water-Gas Shift process, the Steam-In process and the Steam Referring process. These processes are objectionable because of their demand for fossil fuels. The electrolytic method has limitations and a thermochemical method, as disclosed in Brecher application or a combined thermochemical and electrolytic method for converting or dissociating water into hydrogen and oxygen is preferred. The following Tables I through V present the pertinent data on the conversion of water by various processes.

TABLE I

| T Δ S | Overall Reactions | ΔH 298° k (k cal/mole) | ΔF 298° k (k cal/mole) |
|---|---|---|---|
| 11.6 | $H_2O_{(l)} \rightarrow H_{2(g)} + \frac{1}{2} O_{2(g)}$ | 68/3 | 56.7 |
| 3.2 | $H_2O_{(g)} \rightarrow H_{2(g)} + \frac{1}{2} O_{2(g)}$ | 57.8 | 54.6 |

TABLE II

| T Δ S | Marchetti Mark 1 Process | ΔH° (k cal/mole) | ΔF° 298° k (k cal/mole) | T° (K) |
|---|---|---|---|---|
| −2.5 | $CaBr_{2(s)} + 2 H_2O_{(g)} \rightarrow Ca(OH)_{2(s)} + 2 HBr_{(g)}$ | 23.8 | 26.3 | 1003 |
| −9.8 | $2HBr_{(g)} + Hg_{(l)} \rightarrow HgBr_{2(s)} + H_{2(g)}$ | −23.2 | −13.4 | 473 |
| 7.9 | $HgBr_{2(s)} + Ca(OH)_{2(s)} \rightarrow CaBr_{2(s)} + H_2O_{(g)} + HgO_{(s)}$ | 35.6 | 27.7 | 373 |
| 7.6 | $HgO_{(s)} \rightarrow Hg_{(l)} + \frac{1}{2} O_{2(g)}$ | 21.6 | 14.0 | 673 |
| 3.2 | Overall $H_2O_{(g)} \rightarrow H_{2(g)} + \frac{1}{2} O_{2(g)}$ | 57.8 | 54.6 | 673 |

TABLE III

| T Δ S | Argonne Nitrate Process | ΔH° (k cal/mole) | ΔF° 298° k (k cal/mole) | T° (K) |
|---|---|---|---|---|
| 2.0 | $2HI_{aq} \rightarrow H_{2(g)} + I_{2(s)}$ | 26.7 | 24.7 | 773 |
| (4.1) | $LiNO_{3(aq)} \rightarrow LiNO_{2(s)} + \frac{1}{2} O_2$ | (19.3) | (15.2) | 1073 |
| (−3.5) | $LiNO_{2(s)} \rightarrow LiNO_{2(aq)}$ | (22.9) | 13.9 | 373 |
| (9) | $H_2O_{(l)} + I_{2(s)} + LiNO_{2(aq)} \rightarrow$ $2HI_{(aq)} + LiNO_{3(aq)}$ | (22.9) | 13.9 | 298 |
| 11.6 | Overall $H_2O_{(l)} \rightarrow H_{2(g)} + \frac{1}{2} O_{2(g)}$ | 68.3 | 56.7 | |

TABLE IV

| T Δ S | deBeni Carbon-Iron Process | ΔH 298° k (k cal/mole) | ΔF 298° k (k cal/mole) | T° (K) |
|---|---|---|---|---|
| | $C + H_2O_{(g)} \rightarrow CO_{(g)} + H_{2(g)}$ | 31.4 | 21.8 | 1273 |
| | $CO_{(g)} + 2 Fe_3O_{4(s)} \rightarrow C_{(s)} + 3 Fe_2O_{3(s)}$ | −29.1 | −13.7 | 773 |

TABLE IV-continued

| T Δ S | deBeni Carbon-Iron Process | ΔH | ΔF 298° k 298° k (k cal/mole) | T° (K) |
|---|---|---|---|---|
| | $3\ Fe_2O_{3(s)} \longrightarrow 2\ Fe_3O_{4(s)} + \frac{1}{2}\ O_{2(g)}$ | 55.5 | 46.5 | 1773 |
| | Overall $H_2O_{(g)} \longrightarrow H_{2(g)} + \frac{1}{2}\ O_{2(g)}$ | 57.8 | 54.6 | |

TABLE V

| | T Δ S | Special Process | ΔH | ΔF 298° k 298° k (k cal/mole) | T° (K) |
|---|---|---|---|---|---|
| (a) | −17.13 | $2\ H_2O_{(l)} + SO_{2(g)} \xrightarrow{\text{Electrolytic}} H_{2(g)} + H_2SO_{4(aq)}$ | −9.30 | 7.83 | 298 |
| (b) | 9.93 | $H_2SO_{4(aq)} \xrightarrow{\text{Thermochemical}} H_2SO_{4(l)} + H_2)$ evaporated | 22.99 | 13.06 | 600 |
| (c) | 18.83 | $H_2SO_{4(l)} \longrightarrow H_2O_{(l)} + SO_{2(g)} + \frac{1}{2}\ O_{2(g)}$ | 54.63 | −35.80 | 1200 |
| (d) | 11.6 | Overall $H_2O_{(l)} \longrightarrow H_{2(g)} + \frac{1}{2}\ O_{2(g)}$ | 68.3 | 56.7 | |

In the above tables the subscripts have the following meanings l — liquid
g — gas
s — solid
aq — aqueous (in solution)
ΔH = change in internal energy and is positive if energy is increased and negative if energy is decreased.
ΔF = ΔW = work done in the step such as changing volume under pressure.
T = absolute temperature.
ΔS = change in entropy.
ΔH − ΔF = RΔS.

Figure 12:
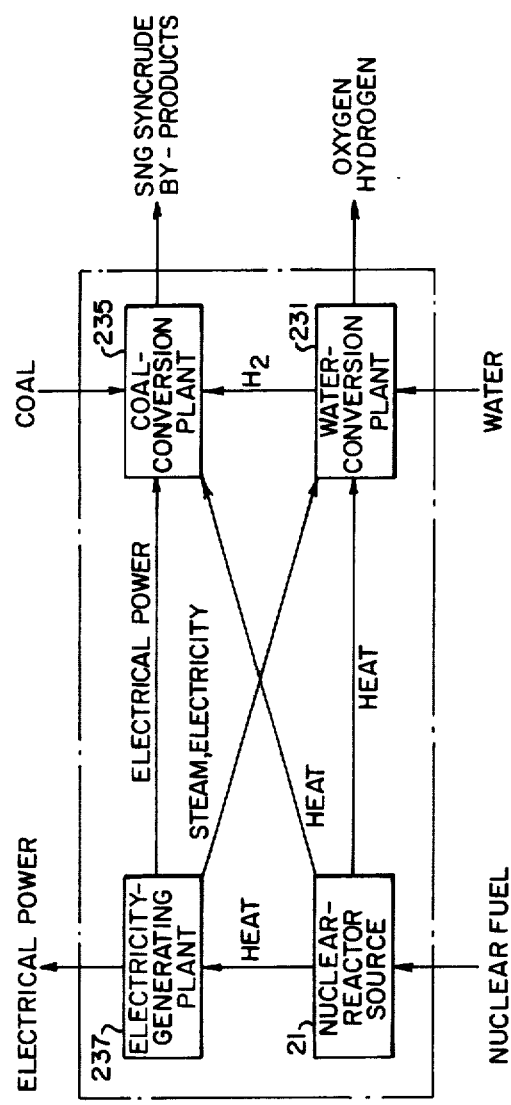
FIG. 12 is a block diagram showing the manner in which the different facilities of apparatus in accordance with this invention are coordinated.

FIG. 12 shows the manner in which the energy from the nuclear-reactor source is used in a water conversion facility according to this invention. The nuclear source 21 supplies energy to the water-conversion plant 231, the coal-conversion plant 235, and the electricity-generating plant 237. The turbines of the latter may be driven directly by the gas from the nuclear reactors 48 (FIG. 3). Unused oxygen and hydrogen are derived from the water-conversion plant 231. Hydrogen from this plant and coal are reacted to produce hydrocarbons in the coal-conversion plant 235. Electrical power for use in the coal-conversion plant 235 and for other purposes is derived from the electricity-generating plant.

Figure 13:
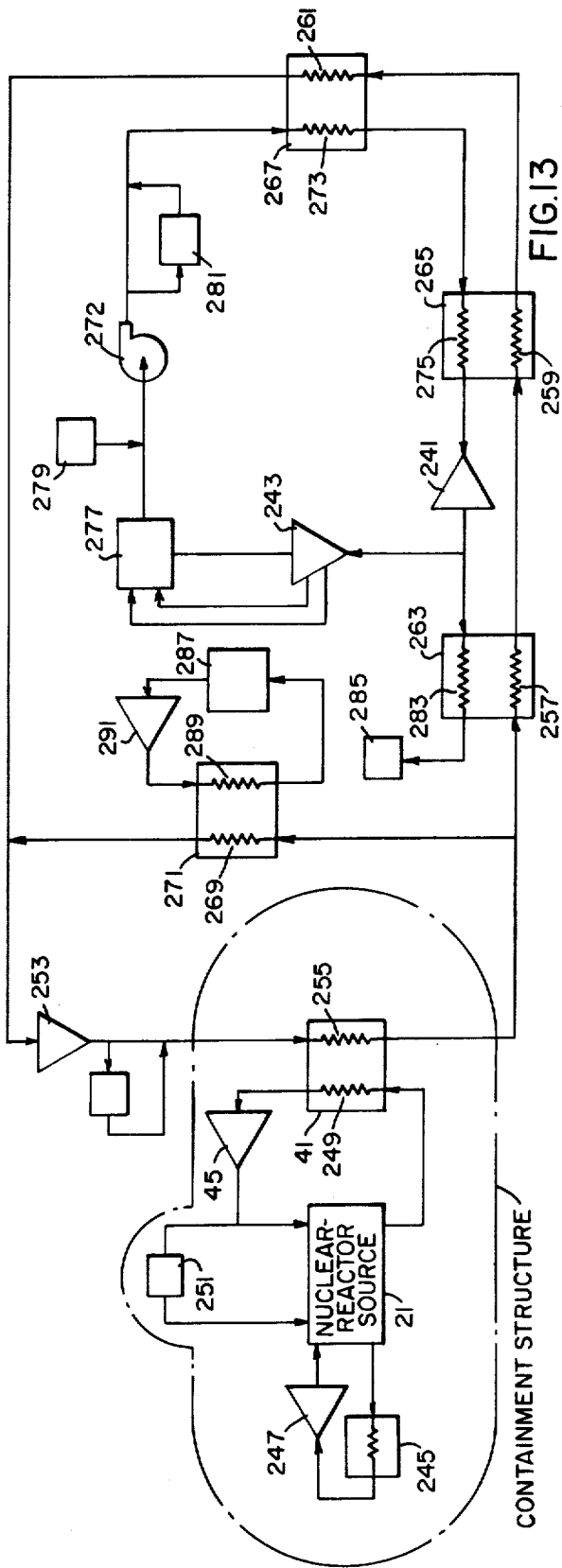
FIG. 13 is a schematic of typical energy transfer apparatus in accordance with this invention.

FIG. 13 shows how the energy from the nuclear source 21 is distributed, in apparatus according to this invention, in which the power is derived through a high-power steam turbine 241 and a low-power extraction steam turbine 243. The source 21 is provided with an emergency cooling heat sink 245 and an emergency cooling circulator 247. The cooling gas from the nuclear source 21 is circulated by the circulator 45 through the primary channel 249 of the intermediate heat exchanger 41. The exit gas from channel 249 is passed through a primary purification purge system 251 to the source 21. The secondary circulator 253 circulates hot gas from channel 255 of heat exchanger 41 through the primary channels 257, 259, 261 of a superheater 263, a steam generator 265 and a feedwater preheater 267 and also through the primary channel 269 of a process-gas heat exchanger 271. Feed-water pump 273 pumps preheated feedwater from the secondary channel 273 of the preheater 267 through the secondary channel 275 of the steam generator 263 and the resulting steam to the turbines 241 and 243. Turbine 243 supplies the low-temperature process 277. Additional feedwater is supplied from source 279. The feedwater analysis is continuously carried out by analyzer 281. Super-heated steam from generator 241 is supplied through secondary channel 283 of superheater 263 to high-temperature process 285. The material processed in high-temperature processor 287 is circulated through secondary channel 289 of heat exchanger 271 by circulator 291.

Figure 14:
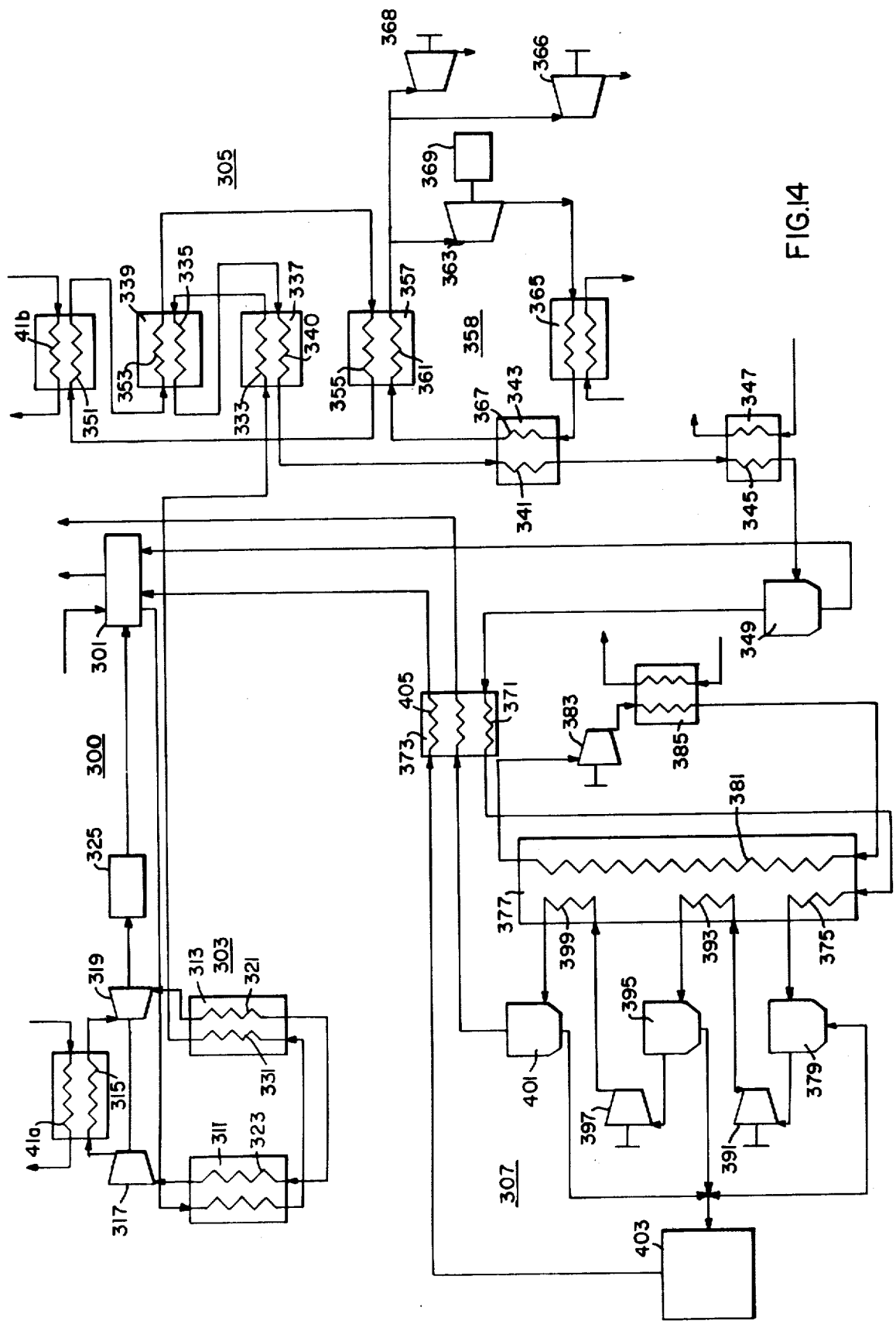
FIG. 14 is a flow schematic of a conversion reactor for converting water into hydrogen and oxygen in the practice of this invention.

The schematic, FIG. 14, shows apparatus for converting water into hydrogen and oxygen by the process disclosed in Brecher application which is called the Special Process and whose reactions are shown in Table V. This apparatus includes an electrolyzer 300, intermediate heat exchangers 41a and 41b, functioning and supplied in the same manner as the intermediate heat exchanger 41 of FIG. 2, an acid preheater 311, an acid vaporizer 313, a sulfuric acid decomposition unit 305, a waste heat recovery unit 358 and a vapor-liquid separator unit 307.

The electrolyzer 300 includes the electrolytic cell unit 301 and DC generator 325. In the electrolytic cell unit 301 reaction (a) of Special Process is carried out producing hydrogen and $H_2SO_{4(aq)}$. The hydrogen is transmitted for use. The $H_2SO_4$ is transmitted to the vaporizer unit 303 to carry out reaction (b) of Special Process and also to vaporize the $H_2SO_4$. This vaporizer unit 303 includes an acid preheater 311 and an acid vaporizer 313. The energy for operating this vaporizer unit is derived from the secondary path 315 of intermediate heat exchanger 41a. The gas from this secondary path is compressed by a compressor 317; the compressed gas is passed through path 315 and expanded in a gas turbine 319 which drives the compressor 317. From the turbine 319 the gas flows through primary paths 321 and 323 of the acid vaporizer 313 and acid preheater 311 back to the compressor 319. The gas turbine 319 also drives an electric generator 325 which supplies energy to the electrolytic cell unit 301. The temperatures at which this gas enters and leaves the components in the gas circuit are shown in flow schematic, FIG. 14.

The acid decomposer 305 includes decomposition reactors 337 and 339. The waste-heat recovery unit 358 includes turbine 363 which drives AC generator 369, and the associated steam generator 357, feedwater preheater 343 and condenser 365. The vapor-liquid separator unit 307 includes vapor-liquid separators 349, 379, 395 and 401, heat exchanger 373, cooler 377, cooler 385 and compressors 383, 391 and 397.

The dehydrated and vaporized $H_2SO_4$ from the vaporizer unit 303 is transmitted from the secondary path 331 of the acid vaporizer 313 through the secondary paths 333 and 335 of the successive decomposition reactors 337 and 339 of the acid decomposer 305, where reaction (c) of Special Process is carried out. The resulting product, including water, $SO_2$ and $O_2$, is passed through the primary path 340 of the decomposition reactor 337, the primary path 341 of the feedwater preheater 343, the primary path 345 of a cooling unit 347 into a vapor-liquid separator 349 of the vapor-liquid separator unit 307 where the $SO_2$ is liquefied under pressure.

Energy is supplied to the decomposition reactors 337 and 339 from the intermediate heat exchanger 41$b$. The gas (He) from the secondary path 351 of this heat exchanger flows through the primary path 353 of decomposition reactor 339, the primary path 355 of a steam generator 357 of the waste-heat recovery unit 358 to the primary path 351.

The secondary path 361 of the steam generator 357 supplies a turbine 363, the exhaust from the turbine 363 flowing through a condenser 365 and the secondary path 367 of the feedwater preheater 343. The turbine drives an AC generator 369 which supplies auxiliary electrical power where needed.

The liquid phase of the vapor-liquid separator 349 includes water and small quantities of $SO_3$ forming weak $H_2So_4$ which is returned to the electrolytic cell unit 301. The $SO_2$ and the $O_2$ from the vapor-liquid separator 349 flows through the primary path 371 of a heat exchanger 373, and a secondary path 375 of a cooler 377 into another vapor-liquid separator 379. The primary path 381 of the cooler 377 is supplied with a cooling gas from a compressor 383 through a cooler 385 where the compressed gas is cooled with water. The compressed gas is expanded in the primary path 381.

The $SO_2$ and $O_2$ of liquid separator 379 is compressed by compressor 391 and passed through a secondary path 393 of cooler 377 into a vapor-liquid separator 395. The gas from separator 395 is compressed by a compressor 397 and passed through another secondary path 399 of cooler 377 into vapor-liquid separator 401. The $SO_2$ is liquefied in vapor-liquid separators 379, 395, and 401 and transmitted to collector 403 whence it is returned to the electrolytic cell 301 through a secondary path 405 of heat exchanger 373.

Figure 15:
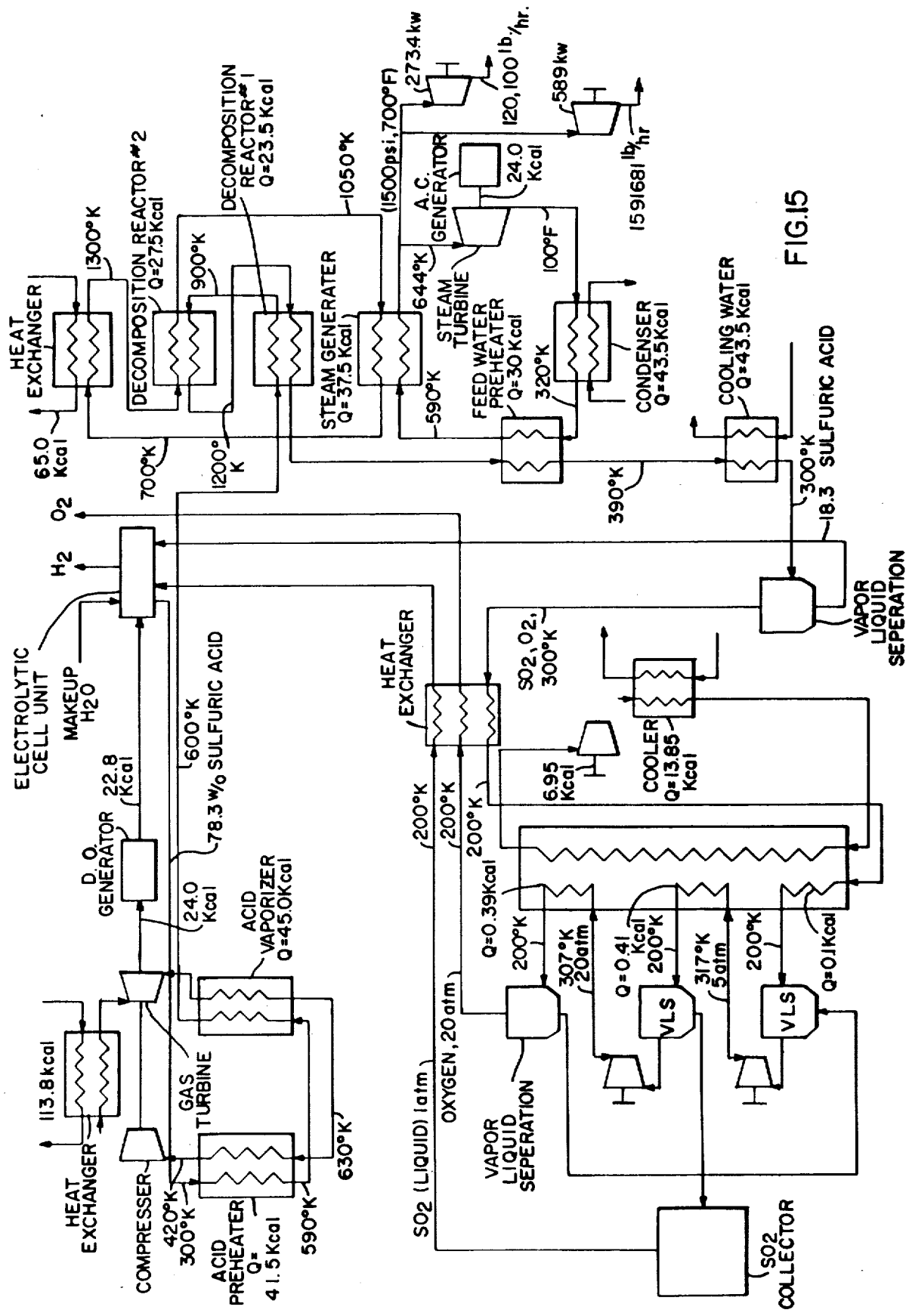
FIG. 15 is a flow schematic similar to FIG. 14 but showing the heat quantities consumed and, the temperature and the flow components.

FIG. 15 shows heat quantities and other parameters. The heat quantities are in kilocalories per gram mole of water decomposed; the Q's presented are the heat duty cycles per mole of water decomposed and per mole of 2 grams of hydrogen produced. The concentration of the sulfuric acid in weight percent, w/o, and the gas flow is in cubic feet per minute (cfm) per mold of water decomposed. FIG. 15 does not show the pumps and other components which are included in the flow circuits.

While preferred embodiments and preferred practice of this invention have been disclosed herein, many modifications thereof are feasible. This invention is not to be restricted except insofar as is necessitated by the spirit of the prior art.

I claim:

1. Apparatus for converting coal and water into at least one hydrocarbon including, a nuclear reactor for supplying energy for said apparatus, a first chemical reactor, reactive with the water, for converting water into hydrogen and oxygen, said first chemical reactor including means for separating said hydrogen and oxygen, means for supplying water to said chemical reactor, connecting means connecting said nuclear reactor to said chemical reactor for supplying energy to said chemical reactor to effect the conversion of said water into hydrogen and oxygen, a second chemical reactor for reacting hydrogen and coal to convert hydrogen and coal into said hydrocarbon, means connected to said second chemical reactor for supplying said coal to said second chemical reactor, and means connected to said first chemical reactor for supplying the hydrogen converted by said first chemical reactor to said second chemical reactor to react with said coal.

2. The apparatus of claim 1 wherein the nuclear reactor is a high-temperature gas-cooled nuclear reactor and the connecting means includes means for deriving energy by heat exchange from the cooling gas of said nuclear reactor for energizing the first chemical reactor.

3. The apparatus of claim 2 wherein the deriving means includes heat-exchange means interposed between the nuclear reactor and the first chemical reactor for isolating the cooling gas from said chemical reactor.

4. The apparatus of claim 1 wherein residual coal remains from the reaction of coal and hydrogen in the second chemical reactor, the said apparatus including a third chemical reactor for reacting coal with oxygen to produce carbon monoxide, means connected to the first chemical reactor for supplying oxygen to said third chemical reactor, means connected to said second chemical reactor for supplying said residual coal to said third chemical reactor to react with said oxygen to produce carbon monoxide, the said apparatus also including a fourth chemical reactor for reacting carbon monoxide with hydrogen to produce a hydrocarbon, means connected to said third chemical reactor for supplying the carbon monoxide produced thereby to said fourth chemical reactor, and means connected to said first chemical reactor for supplying said hydrogen to said fourth chemical reactor to react with said carbon monoxide to produce a hydrocarbon.

5. The apparatus of claim 4 wherein the hydrogen-supplying means is connected to the first chemical reactor through the second chemical reactor, the hydrogen supplied to the fourth chemical reactor being excess hydrogen derived from the second chemical reactor.

* * * * *